US012618106B2

(12) United States Patent
Lissandrello et al.

(10) Patent No.: US 12,618,106 B2
(45) Date of Patent: May 5, 2026

(54) METHODS AND SYSTEMS FOR EXTRACTION, PROCESSING, AND DETECTION OF NUCLEIC ACIDS

(71) Applicant: The Charles Stark Draper Laboratory, Inc., Cambridge, MA (US)

(72) Inventors: Charles A. Lissandrello, Natick, MA (US); Aditi R. Naik, Hollis, NH (US); Diana J. Lewis, Cambridge, MA (US); Erin Rosenberger, Quincy, MA (US); Joseph Neil Urban, Cambridge, MA (US); Jason Fiering, Boston, MA (US); Caleb R. Bell, Cambridge, MA (US); Cait Ni Chleirigh, Cambridge, MA (US); Ernest Kim, Cambridge, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 467 days.

(21) Appl. No.: 18/141,553

(22) Filed: May 1, 2023

(65) Prior Publication Data

US 2024/0002919 A1      Jan. 4, 2024

Related U.S. Application Data

(60) Provisional application No. 63/367,516, filed on Jul. 1, 2022.

(51) Int. Cl.
*C12Q 1/6851*          (2018.01)
*B01L 3/00*            (2006.01)
                       (Continued)

(52) U.S. Cl.
CPC ...... *C12Q 1/6851* (2013.01); *B01L 3/502715* (2013.01); *B01L 7/52* (2013.01);
                       (Continued)

(58) Field of Classification Search
None
See application file for complete search history.

(56) References Cited

U.S. PATENT DOCUMENTS

2016/0320307 A1*  11/2016  Horii ................ G01N 35/00029
2018/0243739 A1*   8/2018  Schenk zu Schweinsberg ..........
                                                      B01L 3/5029
2019/0291110 A1*   9/2019  Liu ................... B01L 3/502738

FOREIGN PATENT DOCUMENTS

WO      WO-2009149115 A1 * 12/2009   .......... B01L 3/50273

* cited by examiner

*Primary Examiner* — Aaron A Priest
(74) *Attorney, Agent, or Firm* — Brooks Kushman P.C.

(57) ABSTRACT

A removable cartridge to be used in a system for extracting and detecting nucleic acids from heterogeneous samples includes a plurality of reservoirs defining at least a first wash buffer reservoir for holding a first wash buffer and a microfluidic assembly configured to attach to the plurality of reservoirs. The microfluidic assembly includes at least one sample reservoir and a nucleic acid extraction matrix in fluid communication to an automated sample preparation (ASP) reservoir through a first flow channel defined by the microfluidic assembly. An assay chamber is in fluid communication with a third flow channel and with the waste reservoir through a fourth flow channel such that a labeled nucleic acid-containing sample flows through the assay chamber and then to the waste reservoir, wherein vibration-driven mixing agitates fluids while present in the assay chamber. Finally, a nucleic acid-detecting microarray module is positioned in the assay chamber.

34 Claims, 23 Drawing Sheets

(51) Int. Cl.
    B01L 7/00         (2006.01)
    *C12Q 1/6806*      (2018.01)

(52) U.S. Cl.
    CPC ....... *B01L 2200/04* (2013.01); *B01L 2200/16*
        (2013.01); *B01L 2300/0636* (2013.01); *B01L*
          *2300/0877* (2013.01); *B01L 2300/0883*
        (2013.01); *B01L 2300/18* (2013.01); *C12Q*
        *1/6806* (2013.01); *C12Q 2600/16* (2013.01)

40 42

36

10

14

12

156

168

Glass lid-500 μm

Grace Biolabs Gasket - 145 μm

Polycarbonate lid- 254 μm

Gasket standoffs- 1.59 mm

Polycarbonate Base- 6.17 mm

Clear PSA - 120 μm

Polycarbonate lid- 254 μm

METHODS AND SYSTEMS FOR EXTRACTION, PROCESSING, AND DETECTION OF NUCLEIC ACIDS

CROSS-REFERENCE TO RELATED APPLICATIONS

This application claims the benefit of U.S. provisional application Ser. No. 63/367,516 filed Jul. 1, 2022, the disclosure of which is hereby incorporated in its entirety by reference herein.

STATEMENT REGARDING FEDERALLY SPONSORED RESEARCH OR DEVELOPMENT

This invention was made with Government support under Contract No. N66001-21-C-4048, awarded by the U.S. Defense Advanced Research Projects Agency (DARPA). The Government has certain rights in the invention.

TECHNICAL FIELD

In at least one aspect, the present invention is related to methods and equipment for extracting and detecting nucleic acids.

BACKGROUND

Nucleic acid extraction from biological samples is typically performed in a laboratory environment using specialized equipment and requiring trained personnel. The often-low abundance of nucleic acid targets in biological samples forces constraints on detection systems including the need for large sample volumes, long incubation durations, and highly-sensitive assays. In addition, system performance may also be limited by the time required for the diffusive motion of targets to their respective probes if there are no means provided to improve transport beyond the diffusion limit.

Sensitive and multiplexed detection of nucleic acid targets from biological samples is also a challenging problem that is typically addressed using specialized equipment in a laboratory setting. The process involves many steps including sample lysis, nucleic acid extraction, nucleic acid detection, and readout. Each of these steps is often achieved using separate pieces of equipment, specialized processing kits, or a sequence of manual steps which require user intervention.

Accordingly, there is a need for improved methods of extracting and detecting nucleic acids.

SUMMARY

In at least one aspect, a removable cartridge to be used in a system for extracting and detecting nucleic acids from heterogeneous samples is provided. The removable cartridge includes a plurality of reservoirs defining at least a first wash buffer reservoir for holding a first wash buffer and a microfluidic assembly configured to attach to the plurality of reservoirs. The microfluidic assembly includes at least one sample reservoir positioned in a first input defined by the microfluidic assembly and a nucleic acid extraction matrix positioned in the microfluidic assembly and in fluid communication to an automated sample preparation (ASP) reservoir through a first flow channel defined by the microfluidic assembly. The microfluidic assembly also includes a waste reservoir defined within the microfluidic assembly and a fluid switching assembly configured to provide a first setting that permits flow from the first wash buffer reservoir through the nucleic acid extraction matrix and then to the waste reservoir and a second setting that permits collection of a nucleic acid-containing sample. An assay chamber is in fluid communication with a third flow channel and with the waste reservoir through a fourth flow channel such that a labeled nucleic acid-containing sample flows through the assay chamber and then to the waste reservoir, wherein vibration-driven mixing agitates fluids while present in the assay chamber. Finally, a nucleic acid-detecting microarray module is positioned in the assay chamber.

In another aspect, a mixing chamber for a removable cartridge used in a system for extracting and detecting nucleic acids from heterogeneous samples is provided. The mixing chamber includes an assay chamber having a pre-determined thickness and a first side having an outer surface and an inner surface. Characteristically, the assay chamber is configured to receive a fluid therein. A vibration motor is affixed to or proximate to the outer surface of the assay chamber. A plurality of air-filled cavities are in contact with both the outer surface wherein the vibration motor is affixed and the fluid being mixed.

In another aspect, a Massively Multiplexed Detection (MMD) Device is provided. The MMD Device is capable of being a fieldable, battery-powered, shelf-stable system which leverages gene-editing technologies and combines novel mechanical elements to achieve highly-multiplexed and sensitive detection of up to 1000 nucleic acid targets. The system is preferably paired with a custom disposable cartridge which contains the assay array and all reagents needed for processing. The system and cartridge together provide an all-in-one sample-to-answer solution for sample lysis, nucleic acid extraction, nucleic acid detection, and readout.

In another aspect, a nucleic acid extraction module includes three or more integrated reagent storage reservoirs (lysis buffer, wash buffer, and elution buffer), three or more passive umbrella valves, one or more pinch valves, a pump or pressure source, one or more motorized rotary valves, a heater, a column for nucleic acid extraction, several microfluidic channels, and connections for sample and reagent inputs, sample output, and waste collection. An integrated computer or microcontroller system provides software controls for the pump, rotary valves, pinch valves, and temperature control. Most components, aside from the pump, pinch valves, heater, and rotary valves, are integrated into a single-use disposable cartridge. The disposable cartridge is fabricated from a multilayer stack of hard plastic materials and adhesives which are laminated together to form the microfluidic path.

In another aspect, with respect to extraction, the present methods and systems enable the automated sample preparation. This extends to a fieldable solution for nucleic acid extraction which can be operated by minimally-trained users and achieves yield equivalent to that of benchtop techniques.

In another aspect, with respect to processing, the present methods and systems encompass a microfluidic mixing component that provides active stirring of the targets leading to enhanced transport and enabling smaller sample volumes, shorter incubation times, and lower limits of detection.

In another aspect, with respect to detection, the present methods and systems can enable a fieldable, battery-powered, shelf-stable system that can provide an all-in-one sample-to-answer solution. The system can be operated by minimally-trained users via a touchscreen interface and requires no intervention throughout the analysis process. The system contains novel elements to maximize nucleic acid yield, enhance target binding to the assay probes, and to achieve sensitive detection via an integrated epifluorescent imaging system.

In another aspect, the present system includes a vibration-motor-driven microfluidic mixing chamber. Both the use of the DC motor to achieve mixing as well as the incorporation of air-filled cavities to enhance local mixing improve performance.

In another aspect, the incorporation of a nucleic acid extraction column in a microfluidic cartridge enables nucleic acid extraction in a closed and automated system. Sufficient drying of the column after the nucleic acids have precipitated out of solution is often important. In the present approach, improved drying and enhanced nucleic acid yield is achieved by flowing air at high velocity and by incorporating a small heater near the extraction column.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIGS. 4C-1, 4C-2, 4C-3, 4C-4, 4C-5, and 4C-6. Schematics showing configurations for the air cavities used for mixing in the assay chamber.

FIGS. 6A, 6B-1, 6B-2, 6C, 6D, 6E, 6F, 6G, 6H, and 6I. Schematics of the layers depicted in FIGS. 5B and 5C.

DETAILED DESCRIPTION

Figure 1A:
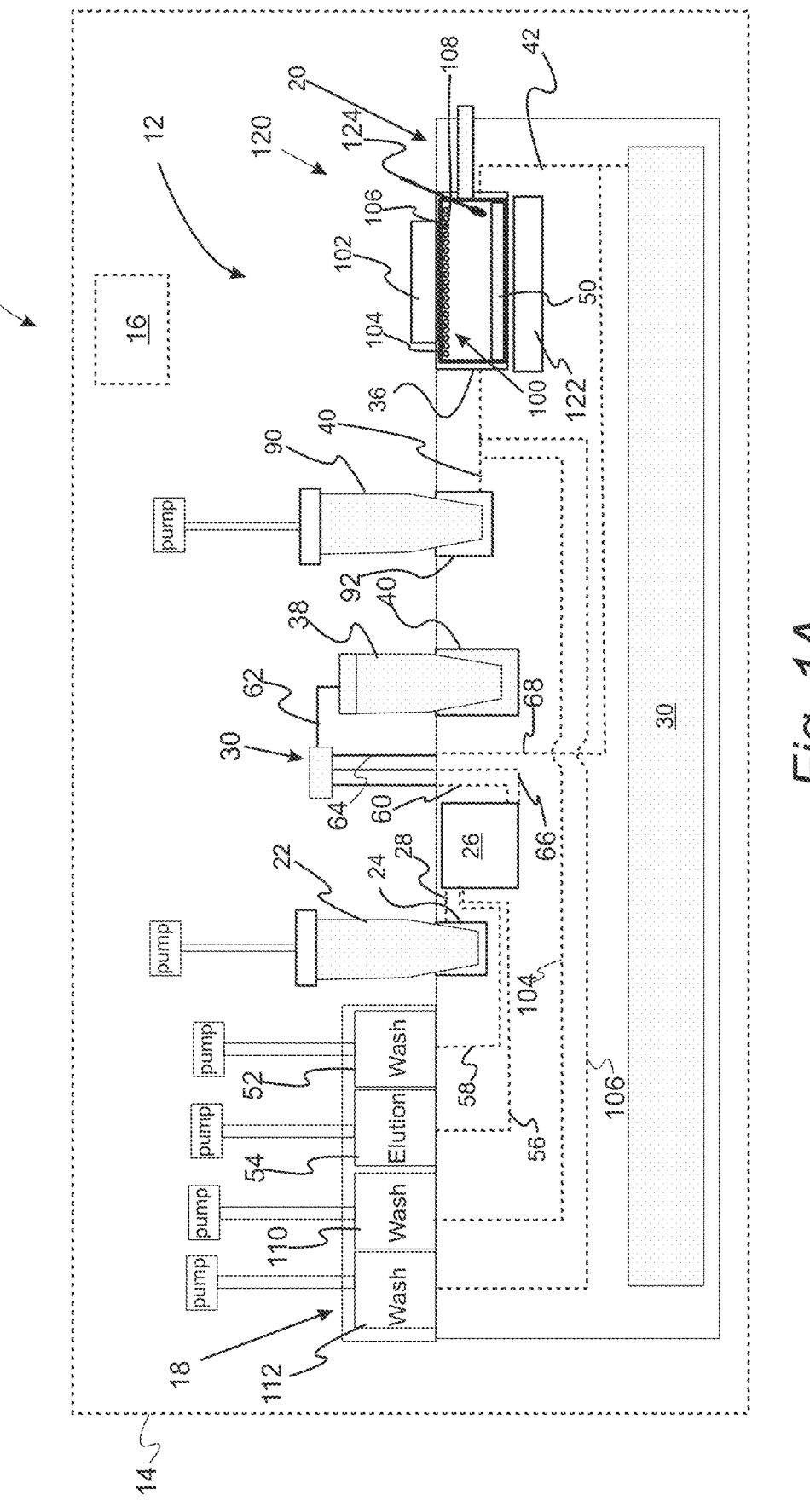
FIG. 1A. Schematic of a system with a removable cartridge for extracting and detecting nucleic acids.

Reference will now be made in detail to presently preferred embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

The phrase "composed of" means "including" or "comprising." Typically, this phrase is used to denote that an object is formed from a material.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits.

When referring to a numerical quantity, in a refinement, the term "less than" includes a lower non-included limit that is 5 percent of the number indicated after "less than." A lower non-includes limit means that the numerical quantity being described is greater than the value indicated as a lower non-included limited. For example, "less than 20" includes a lower non-included limit of 1 in a refinement. Therefore, this refinement of "less than 20" includes a range between 1 and 20. In another refinement, the term "less than" includes a lower non-included limit that is, in increasing order of preference, 20 percent, 10 percent, 5 percent, 1 percent, or 0 percent of the number indicated after "less than."

For any device described herein, linear dimensions and angles can be constructed with plus or minus 50 percent of the values indicated rounded to or truncated to two significant figures of the value provided in the examples. In a refinement, linear dimensions and angles can be constructed with plus or minus 30 percent of the values indicated rounded to or truncated to two significant figures of the value provided in the examples. In another refinement, linear dimensions and angles can be constructed with plus or minus 10 percent of the values indicated rounded to or truncated to two significant figures of the value provided in the examples.

The term "one or more" means "at least one" and the term "at least one" means "one or more." The terms "one or more" and "at least one" include "plurality" as a subset.

The term "substantially," "generally," or "about" may be used herein to describe disclosed or claimed embodiments. The term "substantially" may modify a value or relative characteristic disclosed or claimed in the present disclosure. In such instances, "substantially" may signify that the value or relative characteristic it modifies is within ±0%, 0.1%, 0.5%, 1%, 2%, 3%, 4%, 5% or 10% of the value or relative characteristic.

The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in a software executable object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

As with reference to the Figures, the same reference numerals may be used herein to refer to the same parameters and components or their similar modifications and alternatives. For purposes of description herein, the directional terms "upper," "lower," "right," "left," "rear," "front," "vertical," "horizontal," and derivatives thereof shall relate to the present disclosure as oriented in FIG. 1. However, it is to be understood that the present disclosure may assume various alternative orientations, except where expressly specified to the contrary. It is also to be understood that the specific devices and processes illustrated in the drawings and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise. The drawings referenced herein are schematic and associated views thereof are not necessarily drawn to scale.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Abbreviations:

"ASP" means automated sample preparation.

"MMD" means Massively Multiplexed Detection

"PMMA" means polymethyl methacrylate.

"PC" means polycarbonate.

"PSA" means pressure-sensitive adhesive.

Referring to FIGS. 1A-1B and 2A-2C, schematics of a system with a removable cartridge for extracting and detecting nucleic acids are provided. Nucleic acid detection and extraction system 10 includes a removable cartridge 12 for extracting and detecting nucleic acids from heterogeneous samples. Removable cartridge 12 is disposed in housing 14 which includes control electronics 16 for operating the cartridge and collecting nucleic acid data therefrom. Removable cartridge 12 includes a plurality of reservoirs 18 defining at least a first wash buffer reservoir for holding a first wash buffer. A microfluidic assembly 20 is configured to attach to the plurality of reservoirs. At least one sample reservoir 22 is positioned in a first input 24 defined by the microfluidic assembly. A nucleic acid extraction matrix 26 is positioned in the microfluidic assembly and in fluid communication to an automated sample preparation (ASP) reservoir through a first flow channel 28 defined by the microfluidic assembly. A waste reservoir 30 is defined within the microfluidic assembly. A fluid switching assembly 32 is configured to provide a first setting that permits flow from the first wash buffer reservoir through the nucleic acid extraction matrix and then to the waste reservoir and a second setting that permits collection of a nucleic acid-containing sample. Assay chamber 36 is in fluid communication with a third flow channel 40 and with the waste reservoir 30 through a fourth flow channel 42 such that a labeled nucleic acid-containing sample flows through the assay chamber and then to the waste reservoir. In a refinement, fluorescent labeling is used. Advantageously, vibration-driven mixing agitates fluids while present in the assay chamber 36. A nucleic acid-detecting microarray module 50 is positioned in the assay chamber. In a refinement, removable cartridge 12 has dimensions of about 12" (length)×12" (width)×12.3" (height).

Nucleic acid extraction matrix 26 can be of any number of designs for extracting nucleic acids (e.g., DNA, RNA, etc.). In general, nucleic acid extraction matrix 26 includes materials that reversibly bind to nucleic acids. In a refinement, nucleic acid extraction matrix 26 can be a nucleic acid extraction column. In a refinement, nucleic acid extraction matrix 26 can include nucleic acid extraction beads. In another refinement, the nucleic acid extraction matrix is incorporated in a cylindrical "spin column" which can be in fluid communication with microchannels at its end faces. In a further refinement, the spin column is fabricated by removing excess length from a spin column designed for centrifugation use.

In a variation, a plurality of reservoirs 18 are defined in a reagent storage block that can include a first wash buffer chamber 52 for holding a first wash buffer and an elution chamber 54 for holding an elution buffer. In a refinement, microfluidic assembly 20 is configured to attach to the reagent storage block. In a further refinement, nucleic acid extraction matrix 26 is a nucleic acid extraction column positioned in the microfluidic assembly 20 and in fluid communication to the automated sample preparation (ASP) reservoir 22 through a first flow channel 28 defined by the microfluidic assembly. The nucleic acid extraction matrix 26 is also in fluid communication with the elution chamber 54 through a second flow channel 56 defined by the microfluidic assembly and with the first wash buffer chamber 14 through wash flow channel 58 defined by the microfluidic assembly 20. Waste reservoir 28 is defined within the microfluidic assembly 20.

Figure 4A:
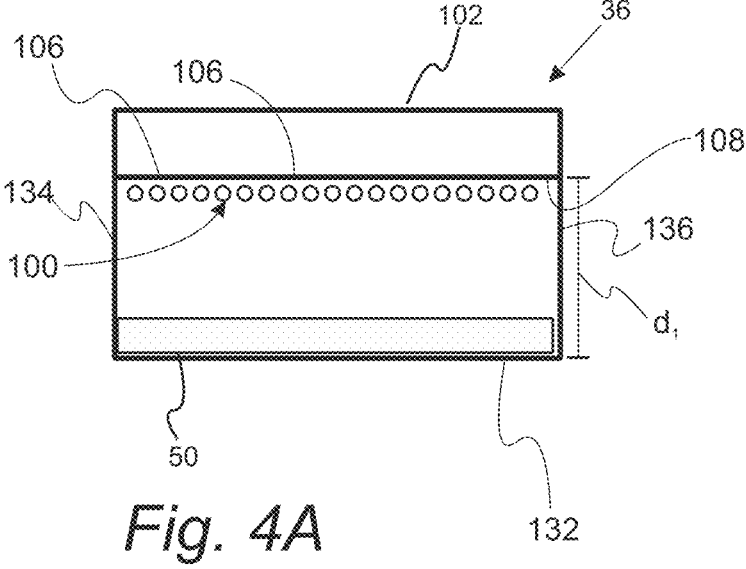
FIG. 4A. Schematic of an assay chamber.
Figure 4B:
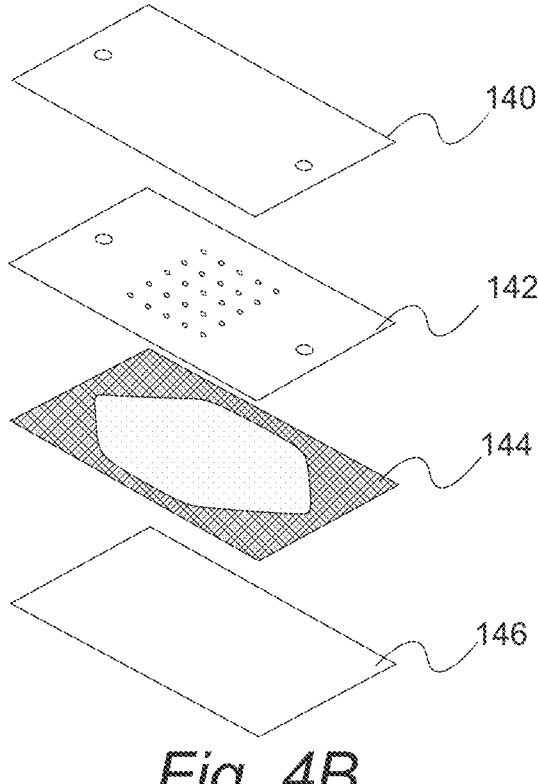
FIG. 4B. Exploded view of an assay chamber.
Figures 1, 2, 3, 4, 4C, 5, 6:
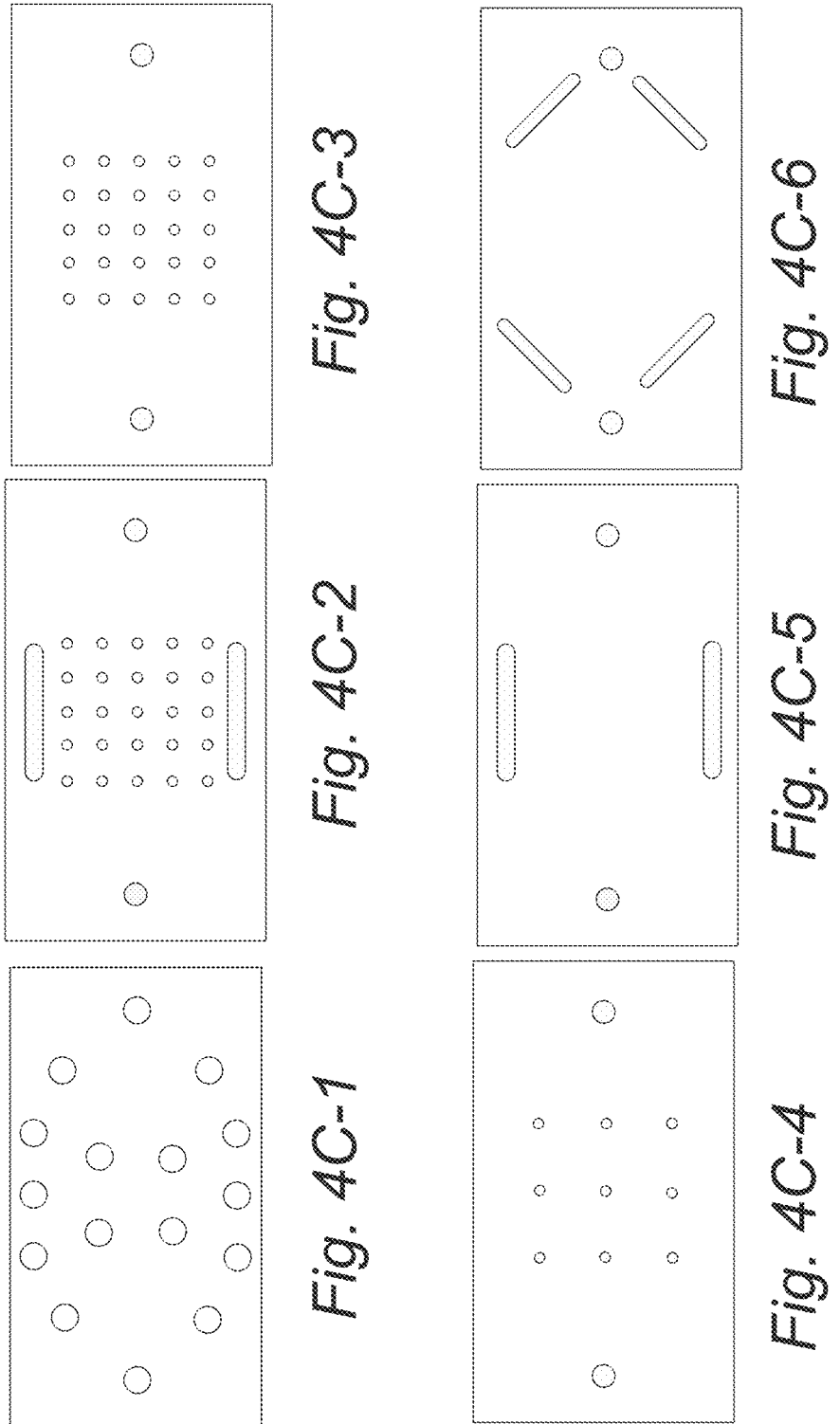

Still referring to FIGS. 1A and 2, an output collection vessel 38 is positioned in port 40 of the microfluidic assembly. Fluid switching assembly 30 is configured to provide a first setting that permits flow from the first wash buffer chamber through the nucleic acid extraction column 26 and then to the waste reservoir 28 through channels 66 and 68 and a second setting that permits flow from a nucleic acid extraction column 26 to the output collection vessel 38 through channels 60 and 62. FIG. 2 depicts a variation of fluid switching assembly 30 in which channel 62 is a flexible tube connecting channel 60 to output collection vessel 38. Pinch valve 70 allows flow through channels 60 and 62 to be closed off. Similarly, channel 64 can be flexible tubing that connects channel 66 to channel 68. Pinch valve 72 allows flow through channel 64 to be closed off. Therefore, in the first setting pinch valve 80 is closed and pinch valve 82 is open and in the second setting pinch valve 80 is open and pinch valve 82 is closed.

Figure 1B:
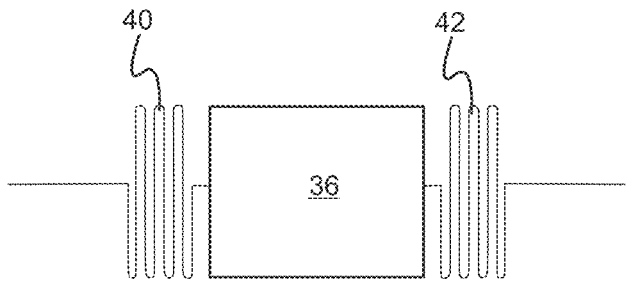
FIG. 1B. Schematic of an assay chamber used in the removable cartridge of FIG. 1A.
Figure 2A:
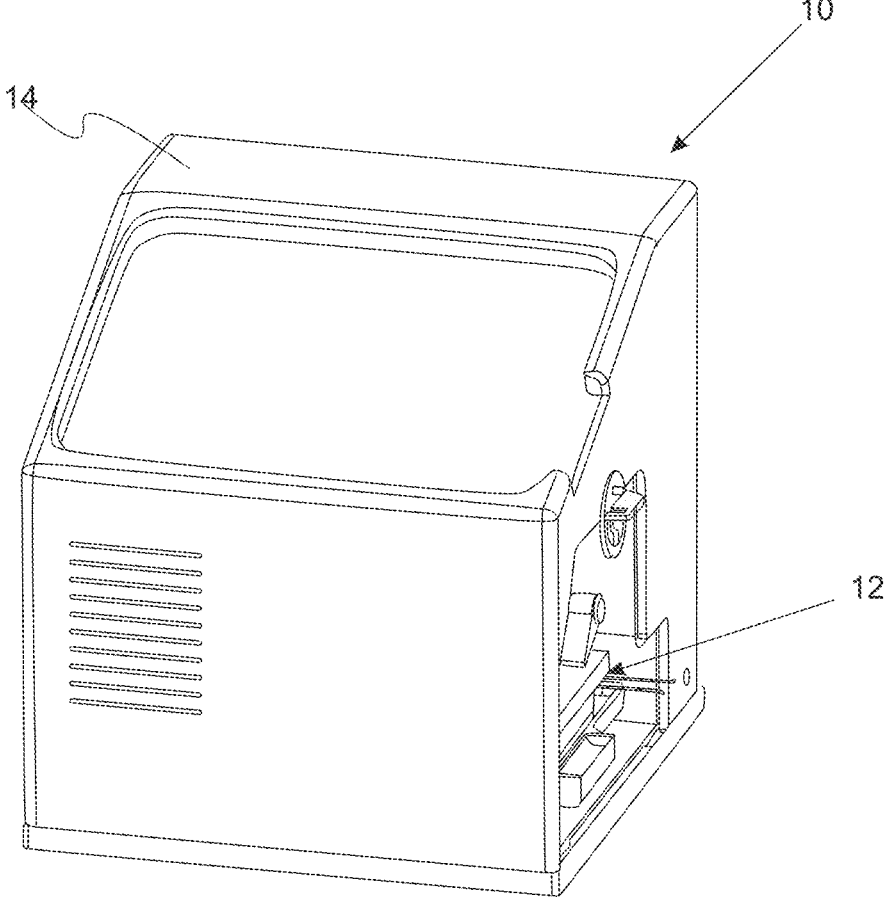
FIG. 2A. Perspective view of a system with a removable cartridge for extracting and detecting nucleic acids.
Figures 2B, 2C:
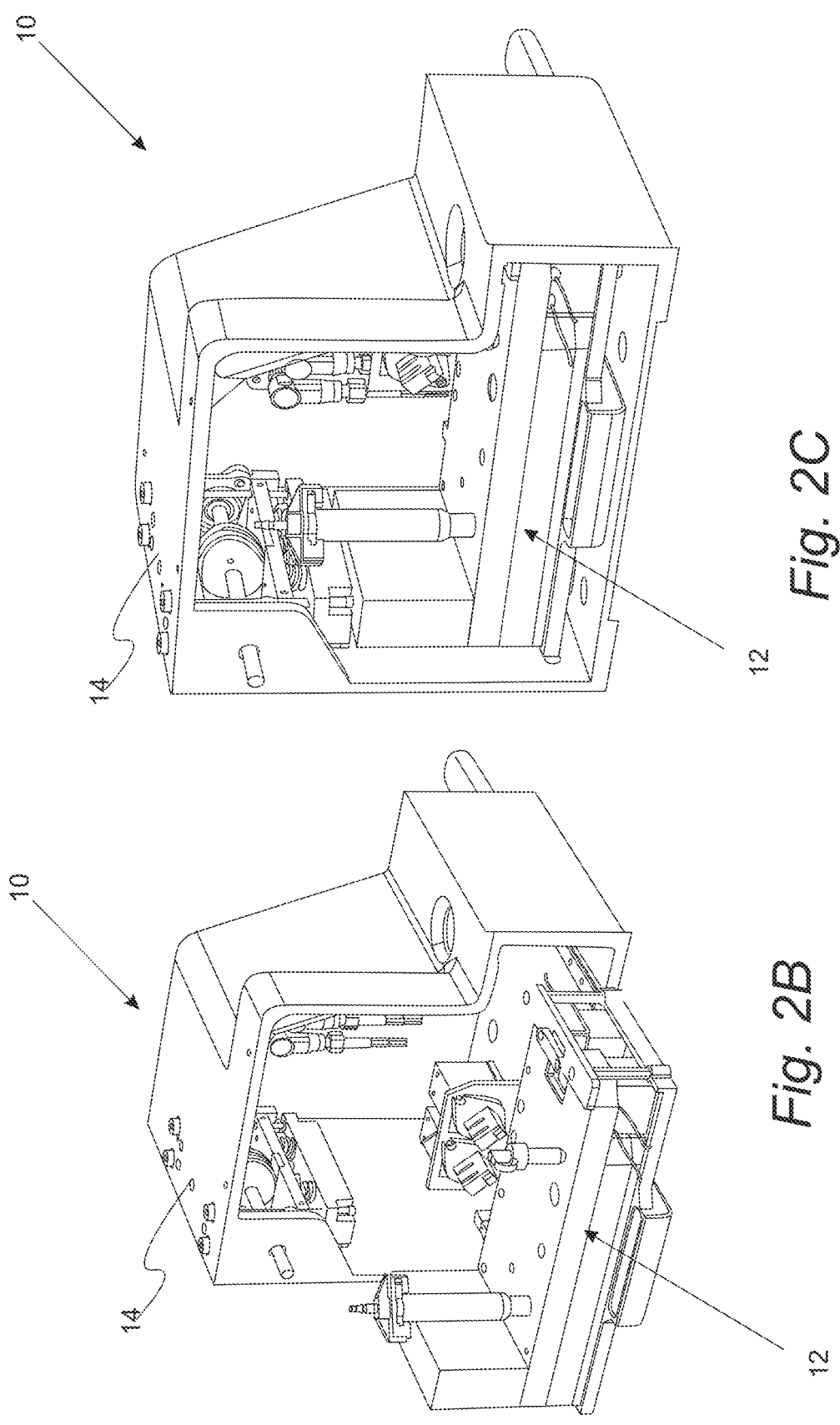
FIG. 2B. Perspective view of a system with a removable cartridge that is retracted FIG. 2C. Perspective view of a system with a removable cartridge that is positioned in the housing.

Assay input vessel 90 is positioned in port 92 of the microfluidic assembly. Assay chamber 36 is in fluid communication with the assay input vessel 90 through a third flow channel 40 and with the waste reservoir 30 through a fourth flow channel 42 such that a labeled nucleic acid sample flows from the assay input vessel 90 through the assay chamber 36 and then to the waste reservoir 30. In a refinement, the third flow channel 40 includes a first serpentine flow channel section and the fourth flow channel 42 includes a second serpentine flow channel section as depicted in FIG. 1B. Advantageously, vibration-driven mixing agitates the labeled nucleic acid sample while present in the assay chamber. Nucleic acid-detecting microarray module 80 is positioned in the assay chamber.

In a variation, a vibration motor 102 is proximate to an outer surface 104 of a first side 106 of the assay chamber, wherein the vibration motor provides the vibration-driven mixing. In a refinement, air-filled cavities 100 are positioned inside the assay chamber contacting an inner surface 108 of the first side of the assay chamber. Advantageously, the vibration motor 102 and the air-filled cavities 100 are configured to promote microfluidic mixing of fluid in the assay chamber 36.

In a variation, a plurality of reservoirs 18 includes a second wash buffer chamber 110 for holding a second wash buffer and a third wash buffer chamber 112 holding a third wash buffer. In a refinement, microfluidic assembly 20 defines a fifth flow channel 114 that is in fluid communication with the second wash buffer chamber 110 and the third flow channel 40. Similarly, microfluidic assembly defines a sixth flow channel 116 that is in fluid communication with the second wash buffer chamber and the third flow channel 40.

In another variation, module 10 includes a closed-loop thermal control system 120 that maintains a steady temperature in the assay chamber. In this regard, the closed-loop thermal control system can include a heater 122 for heating the assay chamber and a temperature probe 124 for measuring the temperature of the assay chamber.

Referring to FIGS. 4A, 4B, and 4C, schematics of assay chamber 36 are provided. FIG. 4A provides a side cross section of the assay chamber. Assay chamber 36 includes sides 106, 132, 134, and 136. Assay chamber 36 has a predetermined thickness $d_1$. First side has an outer surface 104 and an inner surface 108. As described above, the assay chamber is configured to receive a fluid therein. A vibration motor is affixed to or proximate to the outer surface 104 of the assay chamber. Finally, a plurality of air-filled cavities 10 are in contact with both the inner surface 108 wherein the vibration motor is affixed and the fluid being mixed.

FIG. 4B provides an exploded view of an example of assay chamber 36.

Adhesive lid 140 is disposed over acoustic lid 142 which is disposed over adhesive gasket 144. Adhesive gasket 144 is disposed over glass slide 146. Acoustic lid 142 defines openings that create the air cavities used for mixing.

Figure 3:
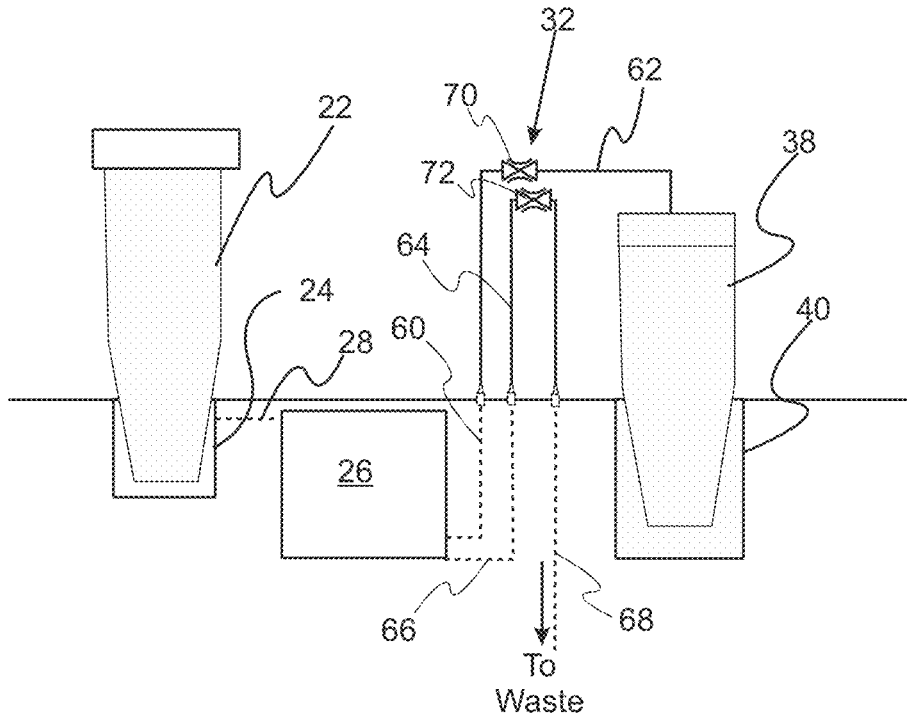
FIG. 3. Schematic of a fluid switching assembly 32.

FIGS. 4C-1 to 4C-6 provide various configurations for acoustic lid 142 and therefore the air cavities. In a refinement, acoustic lid 142 has a width of about 27 mm, a length of about 15 mm, and a thickness of about 0.508 mm. In FIG. 4C-1, circular openings are arranged in the center and along the periphery of the acoustic lid. FIGS. 4C-3 and 4C-4 provide circular openings arrange in rectangular arrays. FIG. 4C-2 provides an example of openings that are a combination of slits and circular openings. FIGS. 4C-5 and 4C-6 provide openings that are slits. In the example of FIG. 4C-1, the pitch can be variable, and the diameter is about 1.35 mm. In the 5×5 array examples of FIGS. 4C-2 and 4C-3, the pitch can be about 1.5 mm and the diameter about 0.5 mm. In the 3×3 array examples of FIGS. 4C-4 and 4C-5, the pitch can be about 4.0 mm and the diameter about 0.5 mm. The slots in FIG. 4C-2 have a width of about 1.0 mm, a length of about 8.0 mm, and a radii of about 0.5 mm. The slots in FIG. 4C-6 have a width of about 1.0 mm, a length of about 5.5 mm, and a radii of about 0.5 mm.

Figure 5A:
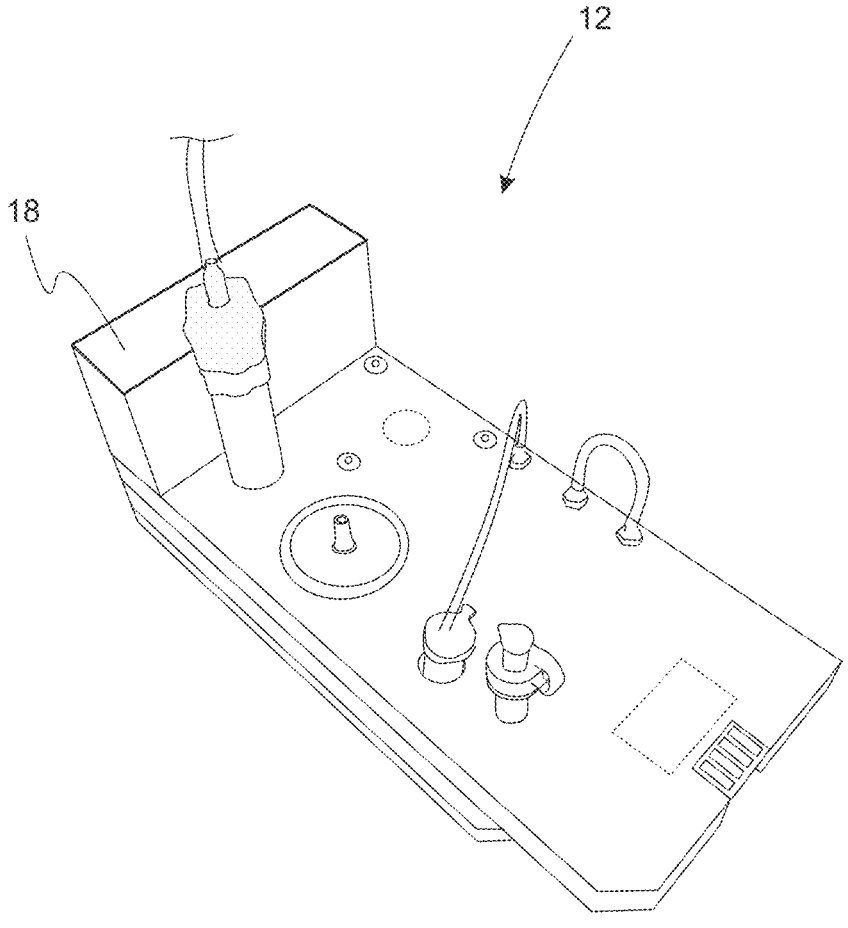
FIG. 5A. Perspective view of a removable cartridge for extracting and detecting nucleic acids.
Figure 5B:
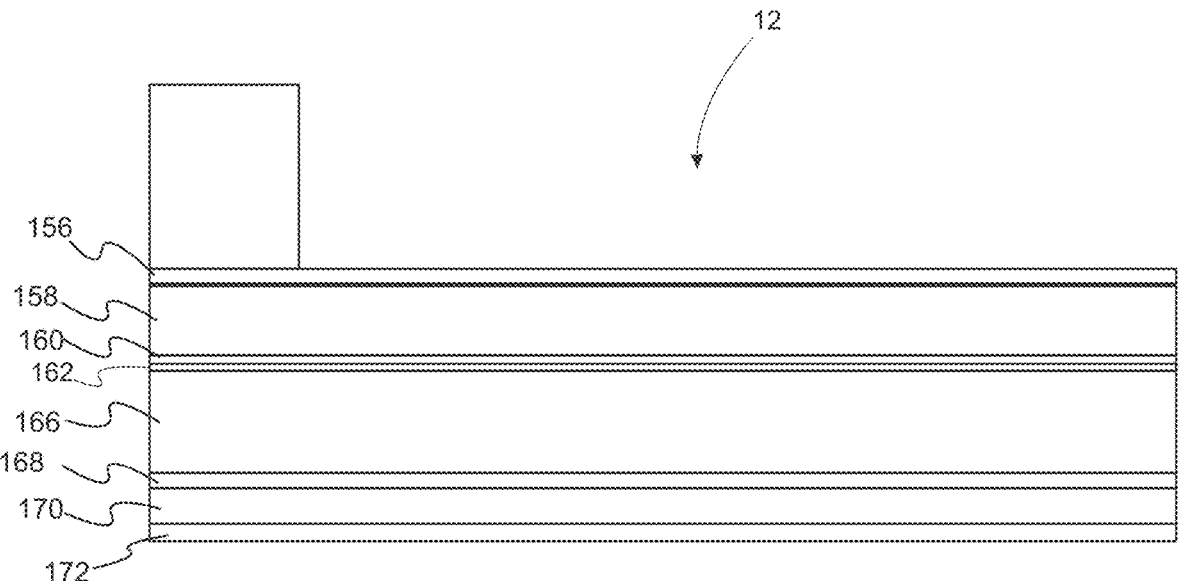
FIG. 5B. Cross section of a removable cartridge for extracting and detecting nucleic acids.
Figure 5C:
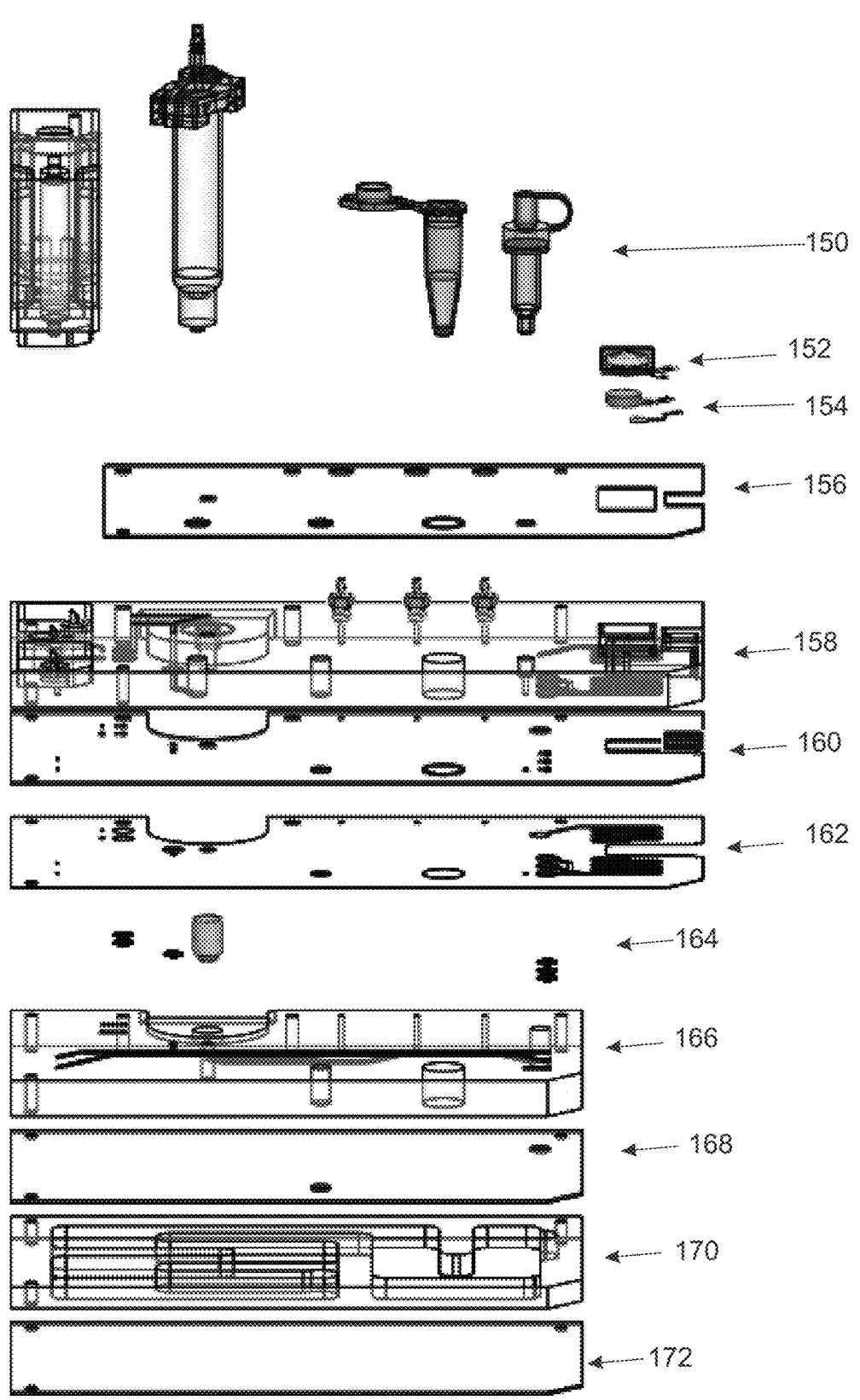
FIG. 5C. Schematic of the multiple layers in a removable cartridge for extracting and detecting nucleic acids.
Figure 6A:
Figure 6A:
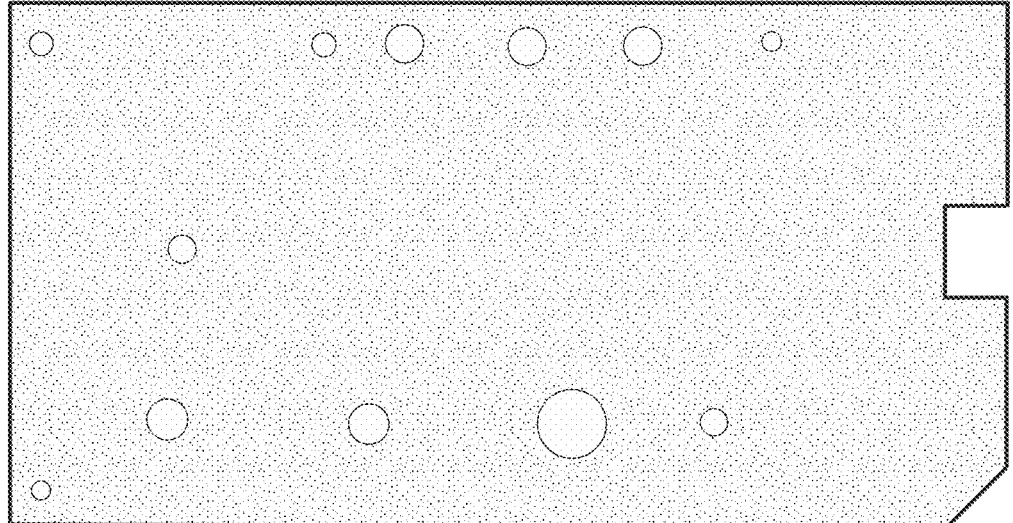
Figures 1, 6B:
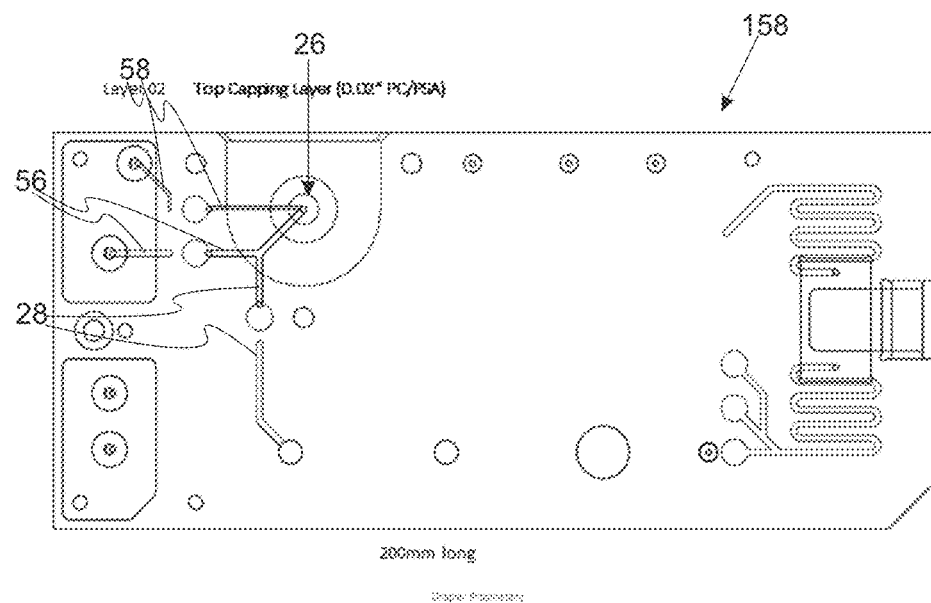
Figures 2, 6B:
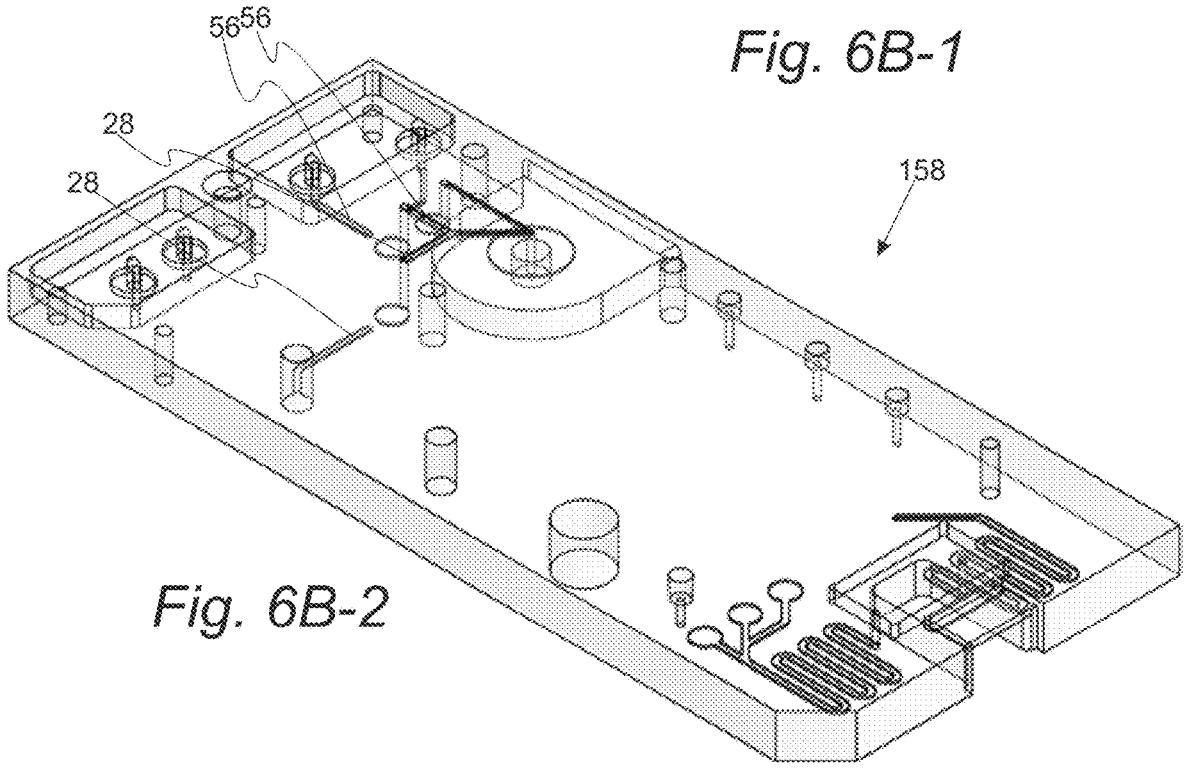
Figure 6C:
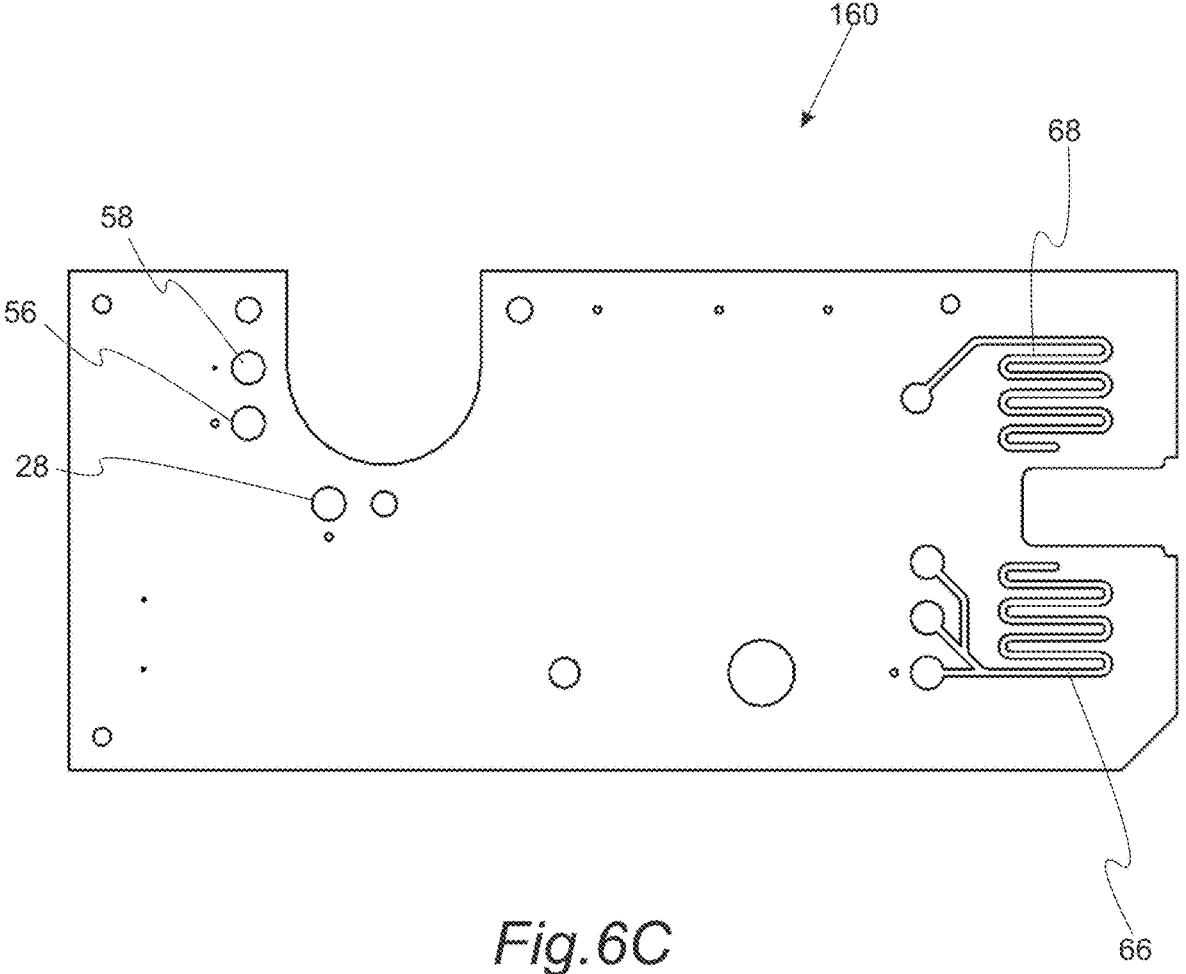
Figure 6D:
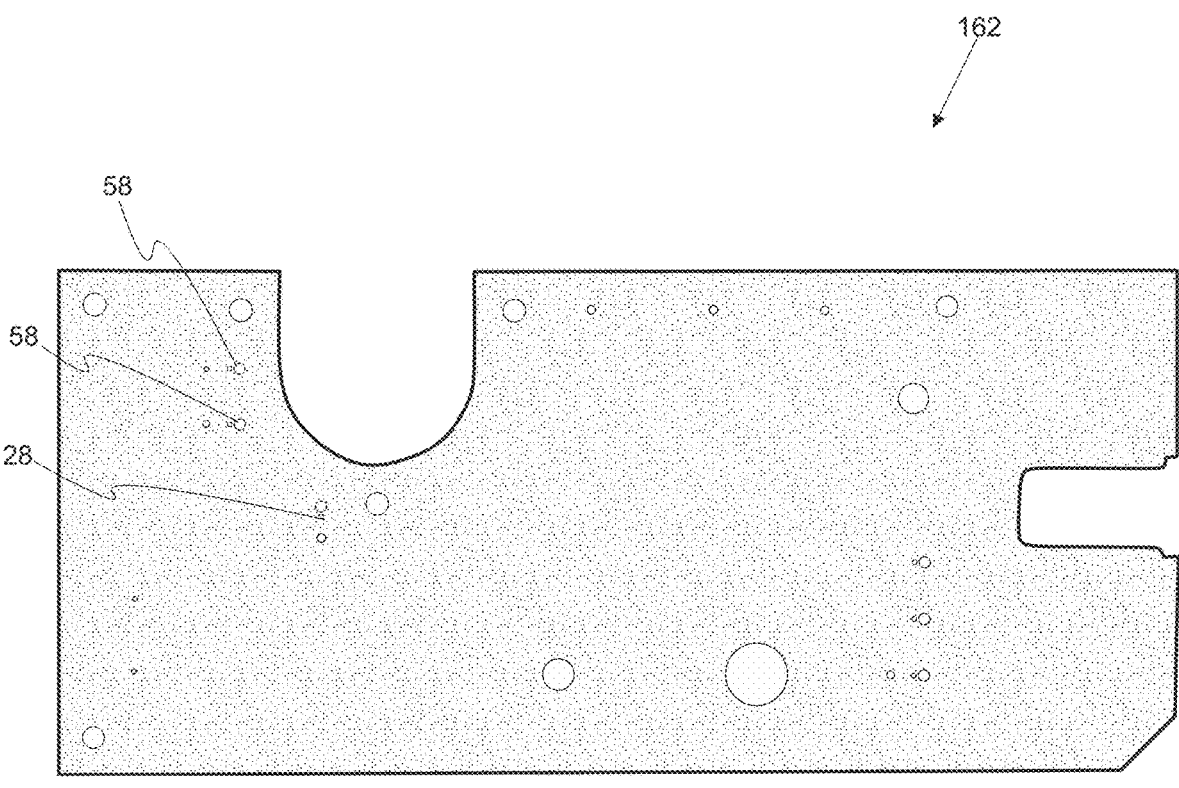
Figure 6E:
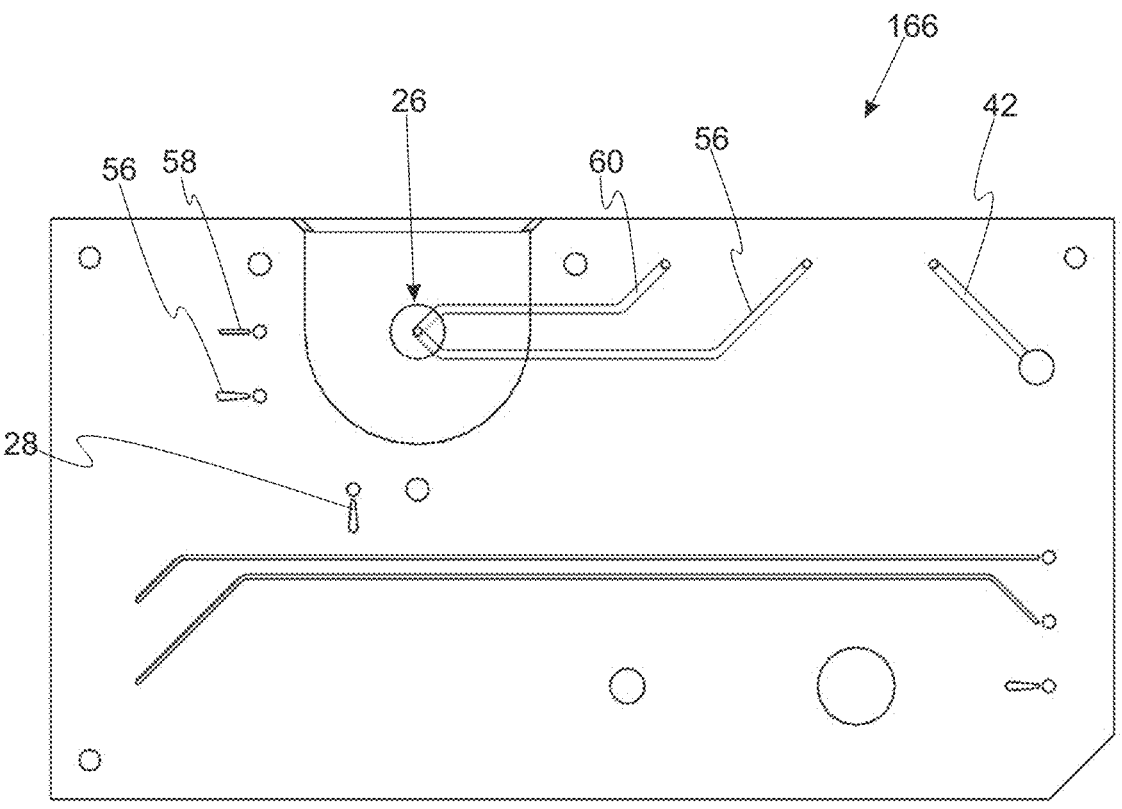
Figure 6F:
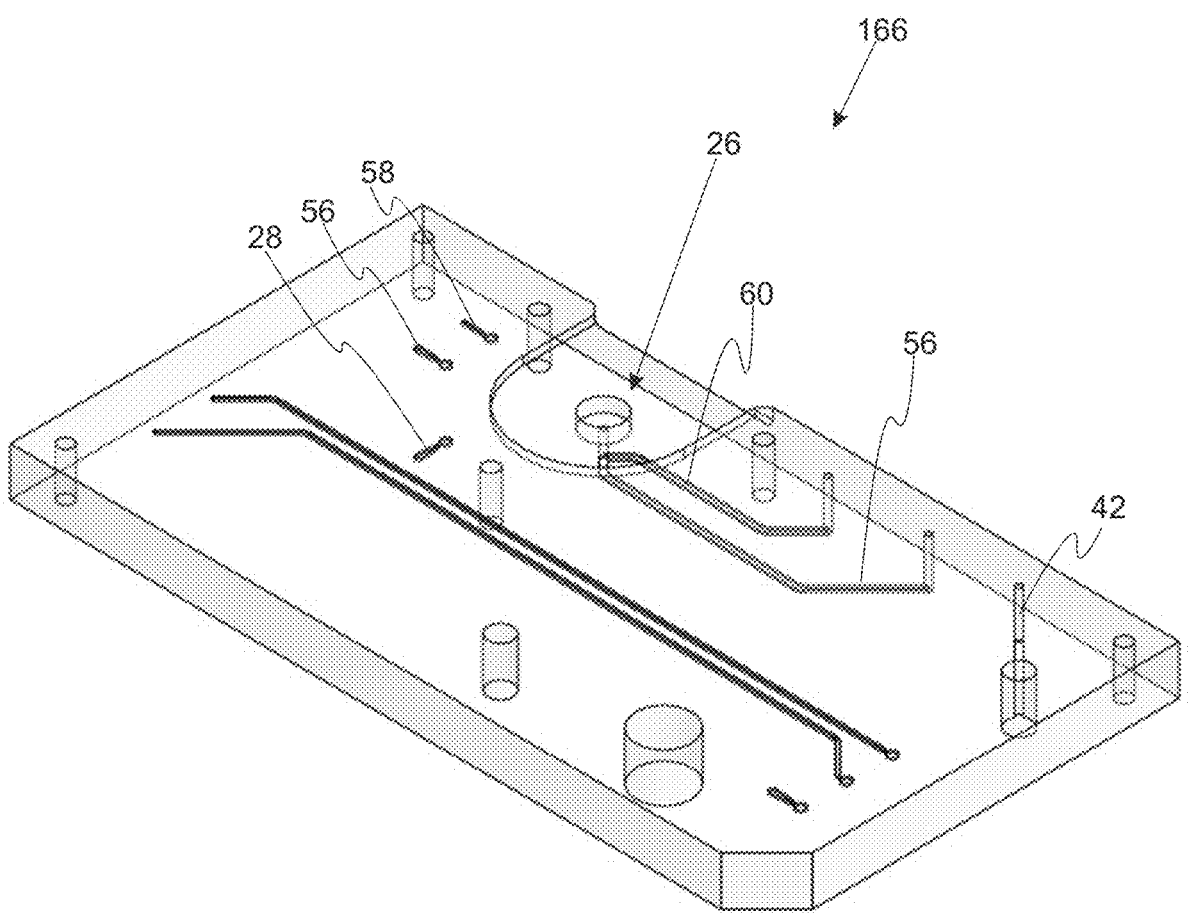
Figure 6G:
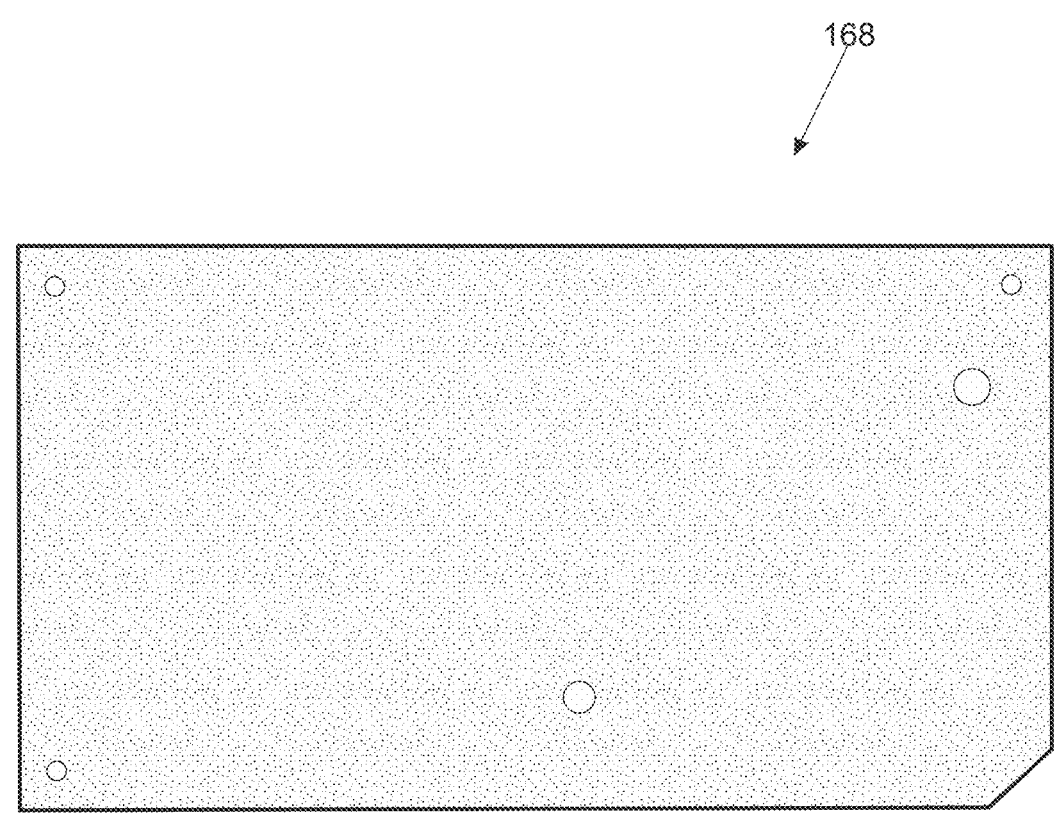
Figure 6H:
Figure 6H:
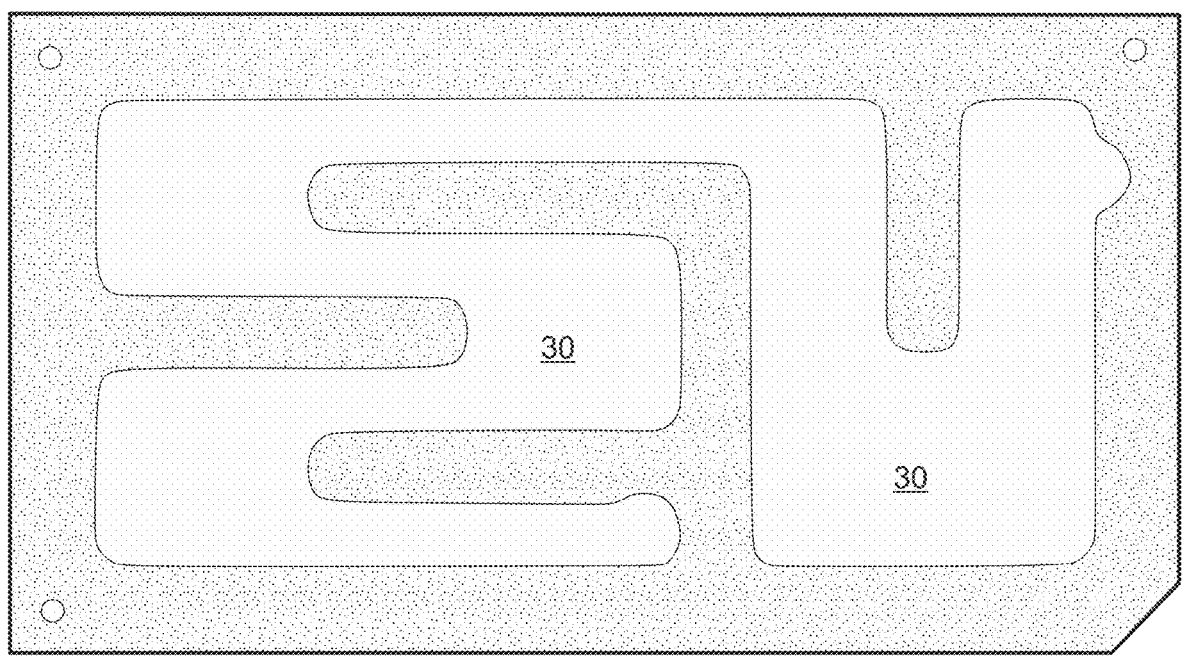
Figure 6L:
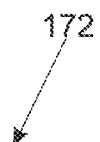
Figure 6L:
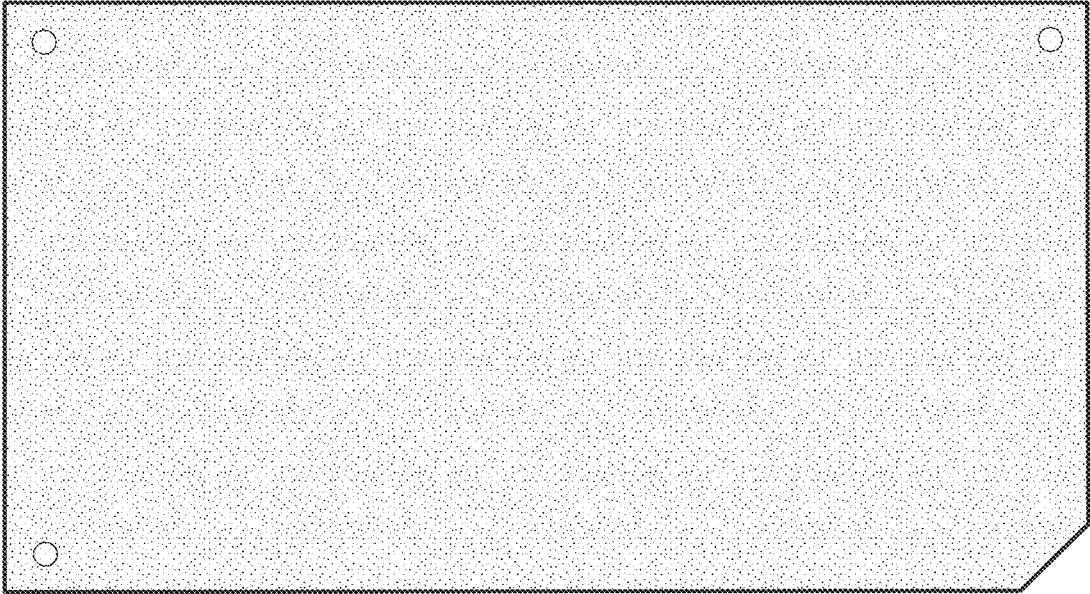

Typically, the microfluidic assembly is composed of a polymer. In particular, the disposable cartridge is fabricated from a multilayer stack of hard plastic materials and adhesives which are laminated together to form the microfluidic path. Suitable polymers include but are not limited to polycarbonate, acrylic (e.g., PMMA), acrylonitrile butadiene styrene, polyethylene terephthalate, nylon, polypropylene, polystyrene, and the like. The microfluidic path, channels and a cutout for the assay chamber can be milled into a rigid polymer base, along with inlet and outlet ports. A laser cutter can used to cut pressure sensitive adhesive (PSA) and a polycarbonate sheet to complete the channels. The assay chamber is formed from laser-cut gasket material, a laser-cut polycarbonate lid (with acoustic cavity holes, if used), and a thin glass lid onto which the assay array has been printed. FIGS. 5A and 5B depict a module, and in particular, a microfluidic assembly that includes multiple polymer layers that define portions of the microfluidic assembly. With reference to FIGS. 5B and 5C, microfluidic assembly 20 includes reagent/sample reservoirs 150, microarray subassembly 152, microarray motor and thermistor 154, top microfluidic layer (e.g., 0.5" PC) 156, top capping layer (0.02" PC/PSA) 158, valve seat layer (e.g., PSA+PC) 160, valve seat layer (PSA) 162, umbrella valves and extraction column 164, bottom microfluidic layer (e.g., 0.5" PC) 166, bottom capping layer (e.g., PSA/PC/PSA) 168, waste bath (Acrylic) 170, and waste batch capping layer (PSA+PC) 172. FIGS. 6A to 6I provide various views of each layer. The channels machined therein and components of FIG. 1A are identified in these figures.

In another embodiment, a method for extracting and detecting nucleic acids with the cartridge set forth above is provided. The method includes a step of a) introducing a nucleic acid sample into the at least one sample reservoir;

b) flowing the nucleic acid sample to the nucleic acid extraction matrix (e.g., column) such that at least a portion of the nucleic acid sample adheres the nucleic acid extraction matrix;

c) flowing the first wash buffer through the nucleic acid extraction matrix and then to the waste reservoir;

d) flowing the elution buffer through the nucleic acid extraction matrix and then to the output collection vessel to collect a purified nucleic acid sample;

e) removing or pumping purified nucleic acid sample from collection vessel to labeling apparatus (e.g., removing the output collection vessel);

f) labeling the purified nucleic acid sample with a label to form a labeled nucleic acid sample;

g) placing a vessel holding the labeled nucleic acid sample into the microfluidic assembly or pumping the labeled nucleic acid sample into the microfluidic assembly;

h) flowing the labeled sample from the vessel holding the labeled nucleic acid sample through the assay chamber and then to the waste reservoir, wherein vibration-driven mixing agitates the labeled sample while present in the assay chamber and closed-loop thermal control maintains steady temperature in the assay chamber; and i) collecting data from the nucleic acid-detecting microarray module.

In a variation, the labeled nucleic acid sample fluorescently labeled. In this situation, system 10 of FIG. 1A can be configured to provide fluorescent read-out capabilities.

Figure 7A:
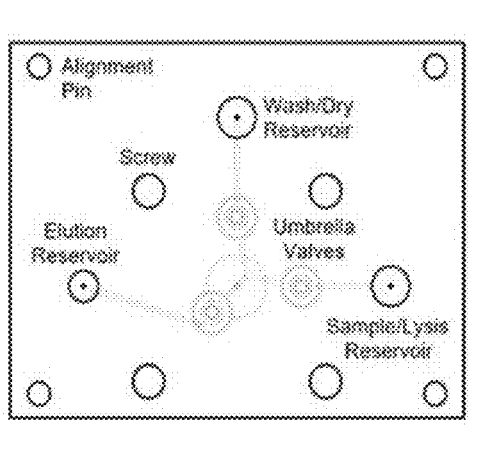
FIGS. 7A and 7B. Exploded view of the top portion of the nucleic acid extraction cartridge.
Figure 7B:
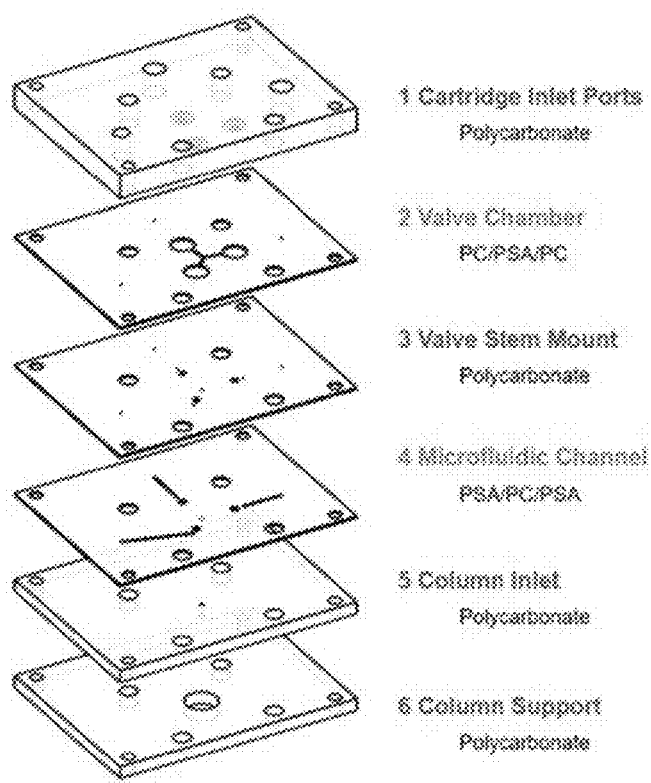
Figures 8A, 8B:
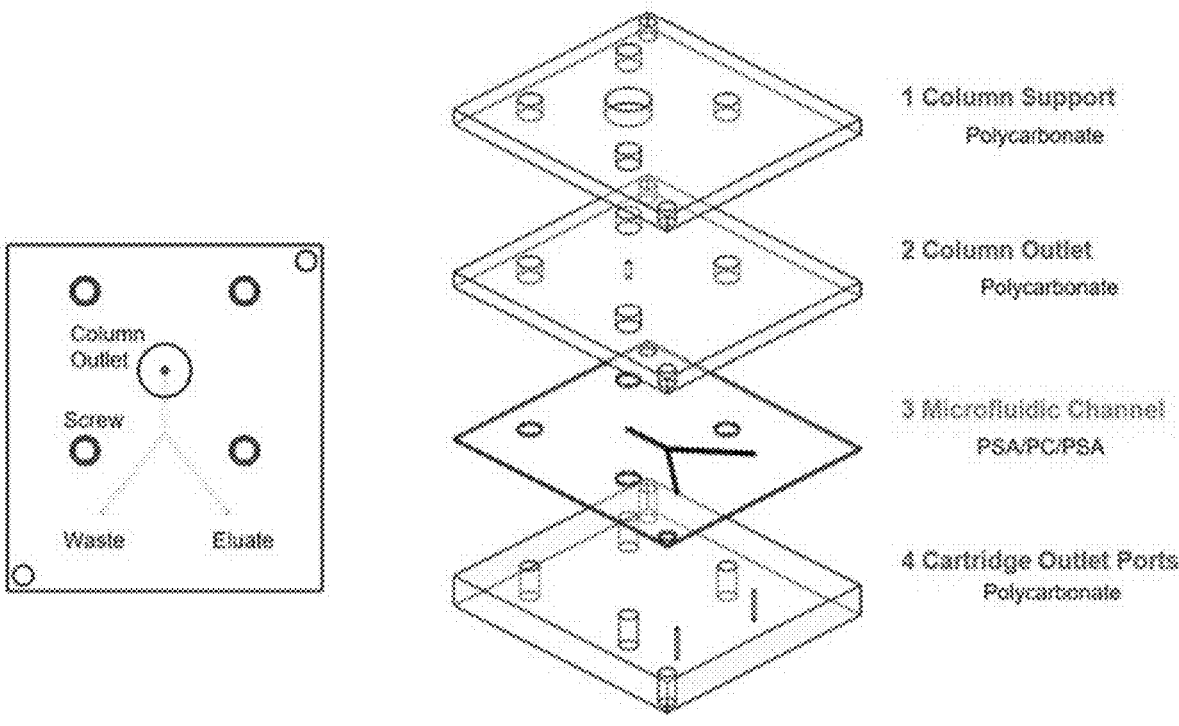
FIGS. 8A and 8B. Exploded view of the bottom portion of the nucleic acid extraction cartridge.
Figures 9A, 9B:
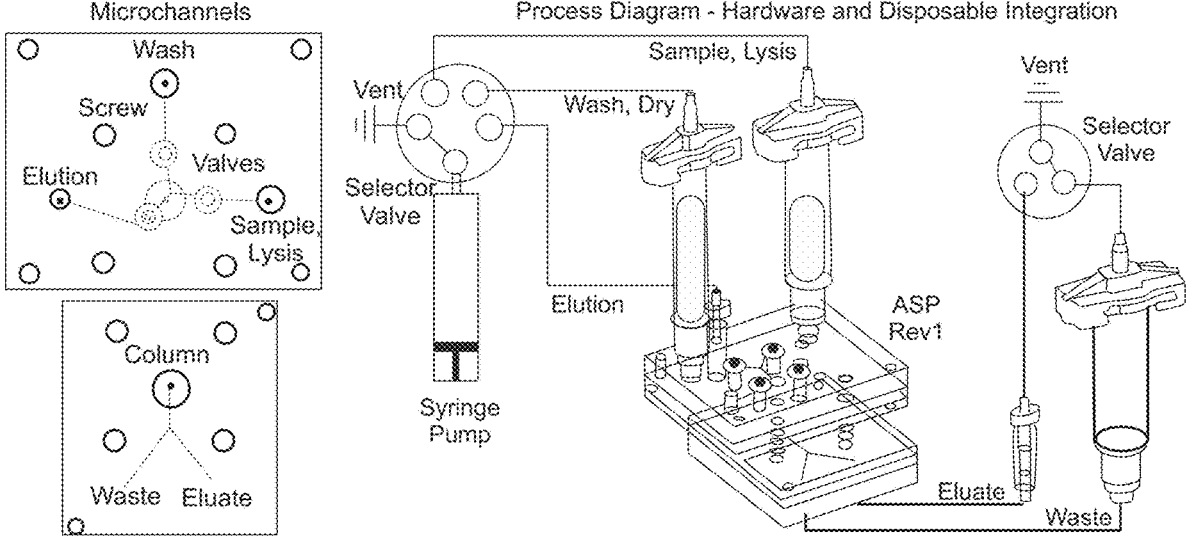
FIG. 9A. Schematic of the key components in the top and bottom portions of the cartridge.
FIG. 9B. Schematic of experimental setup including external pump and rotary valves, tubing connections, reagent reservoirs, collection vessels, and assembled cartridge.

A variation of the nucleic acid extraction cartridge are depicted in FIGS. 7 and 8. The top portion contains the three passive umbrella valves, microfluidic channels, and connections to the three reagent storage reservoirs. The bottom portion contains microfluidic channels and connections to the sample output and waste collection vessels. A nucleic acid extraction column is fit between the top and bottom portions of the cartridge and held in place using two elastomeric gaskets, standoffs, and four screws to form the completed cartridge assembly, as depicted in FIG. 9. The cartridge is built from laser-cut or machined acrylic or polycarbonate base material and the microchannels are created from laser-cut biocompatible pressure-sensitive adhesive and polycarbonate layers. During assembly, the three umbrella valves are pressed into valve locations cut into these laser cut parts and used to prevent reverse flow of fluid into the reservoirs and to help direct flow through the extraction column. Following assembly, the microfluidic parts are laminated under heat and pressure to improve adhesion between the layers. The reservoirs are interfaced directly above the top microfluidic part using Luer and slip connections, and with the bottom microfluidic part with tubing and/or Luer connections. The three reagent reservoirs are prefilled with lysis buffer, wash buffer, and elution buffer, respectively.

The automated sample preparation process begins with the addition of raw sample into the first reservoir, which contains 1.5 ml concentrated lysis buffer and 1.5 ml ethanol. The sample is mixed within the first reservoir for ~30 seconds to lyse the cells, releasing the nucleic acid. The syringe pump is used to fill a 5 ml syringe with ambient air from an input on a rotating selector valve and the air is expelled into the first reservoir, pushing the lysate solution through the extraction column and into a waste reservoir. During this step, the nucleic acid becomes bound to the silica matrix within the extraction column. This step is repeated several times to empty the first reservoir. Next, the selector valve output is switched to the second reagent reservoir, which contains 10 ml wash buffer and ethanol. As described above, the syringe pump is used to push the wash solution through the extraction column and into the waste, removing undesired cellular debris and lysis buffer contamination. Following the wash step, a 10 minute drying step is completed during which the column is heated to ~70 C to remove ethanol from the extraction column. Lastly, the nucleic acid is extracted from the column by pushing 200 μl elution buffer through the column and into an eluate reservoir. The column remains heated during this final step and the elution buffer is allowed to remain within the column for 2-3 minutes to optimize contact between the buffer and the column. To reduce lysis contamination within the eluate, the microchannels can be prefilled with elution buffer prior to beginning the extraction process. The extracted nucleic acid is characterized for quality and quantity using several analytic methods, including spectrophotometry, fluorometry, and qPCR characterization. The entire extraction process from sample to purified nucleic acid can be completed within 15-20 minutes.

The microfluidic mixing module handles the transport of input sample from the nucleic acid extraction module to the assay array. The module comprises a pump or pressure source, several microfluidic channels, a heater, a temperature probe, an assay array, an assay chamber, connections for sample input and sample output, and several components for microfluidic mixing of the fluid in the assay chamber. A miniature vibration motor attached to the surface of the assay chamber generates mechanical excitation which causes motion of the fluid. The assay chamber is mechanically isolated from the rest of the microfluidic module using compliant standoffs to enhance the efficiency of the vibration motor. Air-filled cavities in the roof of the chamber further enhance fluid motion by locally amplifying the mechanical excitation. Custom-developed software controls the pump, the heater, and the vibration motor. The system combines the vibration-driven mixing approach with fluid pumping to achieve high efficiency mixing in the assay chamber. Most components, aside from the pump, are integrated into a single-use disposable cartridge. The disposable cartridge is fabricated from a multilayer stack of hard plastic materials and adhesives which are laminated together to form the microfluidic path.

As set forth above, to create the microfluidic path, channels and a cutout for the assay chamber are milled into a polycarbonate base, along with inlet and outlet ports. A laser cutter is used to cut pressure-sensitive adhesive (PSA) and a polycarbonate sheet to complete the channels. The assay chamber is formed from laser-cut gasket material, a laser-cut polycarbonate lid (with acoustic cavity holes, if used), and a thin glass lid onto which the assay array has been printed.

Figure 10:
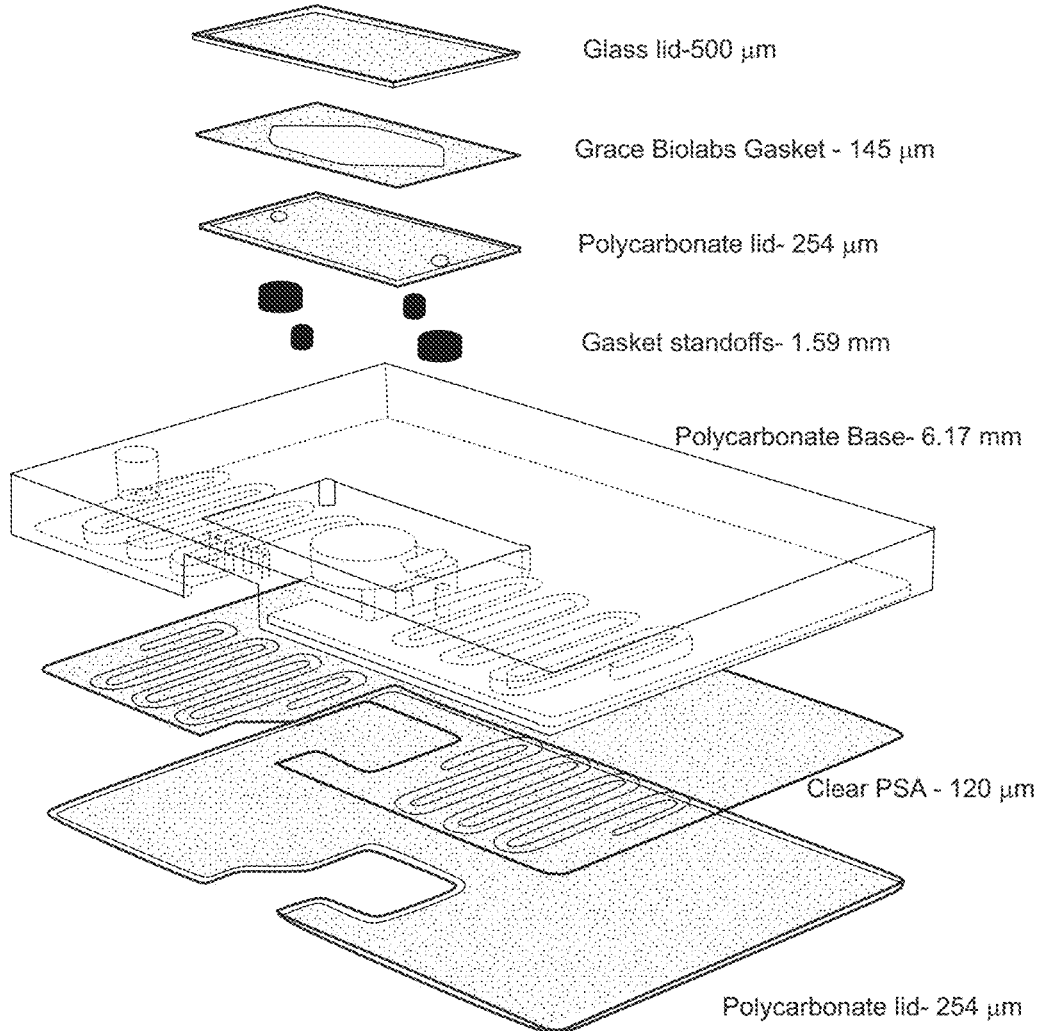
FIG. 10. Exploded view of the microfluidic cartridge including the assay chamber.
Figure 11A:
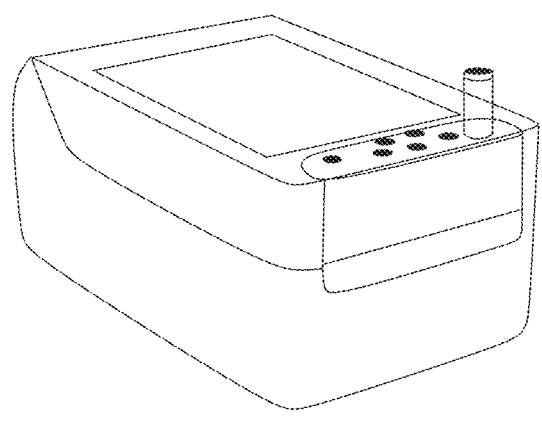
FIGS. 11A and 11B. Perspective view of the prototype integrated system and disposable cartridge of FIGS. 7 to 10.
Figure 11B:
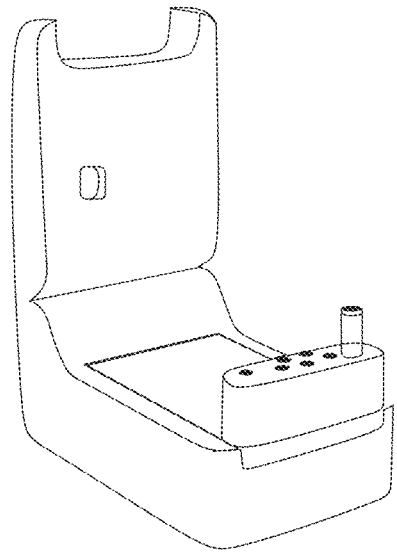

The designs of the microfluidic cartridge and the assay chamber are depicted in FIGS. 4A, 4B, 4C, and 10, respectfully. Prior to the assembly the glass slide and polycarbonate lid are silane treated to provide favorable conditions for liquid filling of the assay chamber. The thickness and shape of the gasket layer determines the internal dimensions of the assay chamber. The cartridge is assembled as follows: the PSA layer is aligned and adhered to the polycarbonate base, and the polycarbonate lid is assembled on top of it. The assay chamber is assembled separately, starting from the glass lid. The gasket is adhered to the glass lid, then the polycarbonate lid is aligned to the gasket and placed on the assembly. With lids that contain acoustic cavities, an additional PSA layer is used to seal the chamber and to allow a flexible surface under the cavities for extra vibration. Several different designs of these lids were fabricated and tested (FIG. 4C) to identify those which provided the best mixing enhancement in the assay chamber. Finally, the gasket standoffs are aligned to the chamber and the base and adhered. The motor and thermistor are adhered onto the assay chamber with PSA, and electrically connected through Pogo pin connections on the cartridge to a durable component. The complete disposable cartridge is shown in FIG. 10, including the vibration motor and thermistor for temperature control.

The general process flow for operating the cartridge of FIGS. 7 to 10 is as follows: The sample is input into a reservoir inserted into one of the cartridge ports. The opposite port is connected through a durable component to a syringe pump, which aspirates a set volume of air from the cartridge to draw in the sample. The cartridge is heated using a resistive heater to bring the sample to 37 C as it passes through the cartridge to the assay chamber. Once the sample is in the chamber, the motor is turned on to mechanically excite the fluid in the assay chamber, causing rapid fluid motion and nucleic acid transport, enhancing interaction with the assay array. This ensures that even low concentrations of nucleic acid targets will interact with the entirety of the assay array. After a specified amount of time the motor is turned off and the assay array is imaged using the fluorescent imaging system. If a sample volume is delivered that exceeds the chamber volume, the pump/mix cycle can be repeated until all the fluid has been processed before turning on the imaging system. Additionally, if a wash step is required, the wash solution can be pumped sequentially into the microarray chamber. The system may be easily reconfigured to accommodate additional reagents by adding more reservoirs and valves to the cartridge.

The MMD device is an integrated, fieldable system that encompasses the modules described above (nucleic acid extraction and microfluidic handling) along with an epifluorescent imaging system, a sensitive, highly-multiplexed detection assay, and a touchscreen interface. The integrated system, depicted in FIG. 112, is ruggedized, battery-powered, and has dimensions of 18.5 cm in length, 12 cm in width, and 8 cm in height. The system comprises a single disposable cartridge that combines the microfluidic mixing and nucleic acid extraction technology described above and a durable system that houses the battery, touchscreen, computer, pump, and imaging system. The system is meant to be easy to use for minimally-trained users. During a typical workflow, the user powers on the system, inserts the disposable cartridge, closes the system (causing alignment of optical and microfluidic elements), inserts the sample or sample vial, and begins the process via the touchscreen interface. Current work supports the processing of nasopharyngeal (NP) swabs and bronchoalveolar lavage (BAL)

samples; however, it is expected that the system and cartridge will be adaptable for use with other sample types.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A cartridge for extracting and detecting nucleic acids from heterogeneous samples comprising:
   a plurality of reservoirs defining at least a first wash buffer reservoir configured to hold a first wash buffer;
   a microfluidic assembly, configured to attach to the plurality of reservoirs, comprising:
      at least one sample reservoir positioned in a first input defined by the microfluidic assembly;
      a nucleic acid extraction matrix positioned in the microfluidic assembly and in fluid communication to an automated sample preparation (ASP) reservoir through a first flow channel defined by the microfluidic assembly,
      a waste reservoir defined within the microfluidic assembly;
      a valve assembly configured to provide a first setting that permits flow from the first wash buffer reservoir through the nucleic acid extraction matrix and then to the waste reservoir and a second setting that permits collection of a nucleic acid-containing sample;
      an assay chamber in fluid communication with a third flow channel and with the waste reservoir through a fourth flow channel, and configured to allow a labeled nucleic acid-containing sample flow through the assay chamber and then to the waste reservoir, wherein a vibration motor is proximate to an outer surface of a first side of the assay chamber, wherein the vibration motor provides vibration-driven mixing, and the assay chamber comprises air-filled cavities inside the assay chamber contacting an inner surface of the first side of the assay chamber, the vibration motor and the air-filled cavities configured to promote microfluidic mixing of fluid in the assay chamber; and
      a nucleic acid-detecting microarray module positioned in the assay chamber.

2. The cartridge of claim 1, wherein the plurality of reservoirs further includes an elution reservoir for holding an elution buffer.

3. The cartridge of claim 2, wherein the nucleic acid extraction matrix is in fluid communication with the elution reservoir through a second flow channel defined by the microfluidic assembly and with the first wash buffer reservoir.

4. The cartridge of claim 1, wherein the microfluidic assembly further includes an output collection vessel positioned in the microfluidic assembly.

5. The cartridge of claim 4, wherein the first setting permits flow from the first wash buffer reservoir through the nucleic acid extraction matrix and then to the waste reservoir and the second setting that permits flow from an elution reservoir to the output collection vessel.

6. The cartridge of claim 1, wherein the microfluidic assembly further includes an assay input vessel positioned in the microfluidic assembly.

7. The cartridge of claim 6, wherein the assay chamber is in fluid communication with the assay input vessel through the third flow channel and with the waste reservoir through the fourth flow channel such that the nucleic acid-containing sample flows from the assay input vessel through the assay chamber and then to the waste reservoir.

8. The cartridge of claim 1, wherein the third flow channel includes a first serpentine flow channel section and the fourth flow channel includes a second serpentine flow channel section.

9. The cartridge of claim 1, wherein the plurality of reservoirs further including a second wash buffer chamber for holding a second wash buffer and a third wash buffer chamber holding a third wash buffer.

10. The cartridge of claim 9, wherein the microfluidic assembly defines a fifth flow channel that is in fluid communication with the second wash buffer chamber and the third flow channel.

11. The cartridge of claim 10, wherein the microfluidic assembly defines a sixth flow channel that is in fluid communication with the second wash buffer chamber and the third flow channel.

12. The cartridge of claim 1, further comprising a closed-loop thermal control system that maintains steady temperature in the assay chamber.

13. The cartridge of claim 12, wherein the closed-loop thermal control system includes a heater for heating the assay chamber and a temperature probe for measuring temperature of the assay chamber.

14. The cartridge of claim 1, wherein the nucleic acid extraction matrix is incorporated in a cylindrical "spin column".

15. The cartridge of claim 14, wherein the spin column is in fluid communication with microchannels at its end faces.

16. The cartridge of claim 14, wherein the spin column is fabricated by removing excess length from a spin column designed for centrifugation use.

17. The cartridge of claim 1, wherein the microfluidic assembly is composed of one or more polymers.

18. The cartridge of claim 17, wherein the microfluidic assembly is composed of a component selected from the group consisting of polycarbonate, acrylic, acrylonitrile butadiene styrene, polyethylene terephthalate, nylon, polypropylene, polystyrene, and combinations thereof.

19. The cartridge of claim 17, wherein the microfluidic assembly includes multiple polymer layers that define portions of the microfluidic assembly.

20. The cartridge of claim 1 wherein a removable heater is mounted to the nucleic acid extraction matrix during use and demounted for disposal of the cartridge.

21. The cartridge of claim 1 configured to be positioned in a control housing to form a system that includes control electronics for operating the cartridge and collecting nucleic acid data therefrom.

22. The cartridge of claim 21, wherein the system is configured to provide fluorescent read-out capabilities.

23. A method for extracting and detecting nucleic acids with a cartridge comprising:
   a plurality of reservoirs defining at least a first wash buffer reservoir for holding a first wash buffer;
   a microfluidic assembly configured to attach to the plurality of reservoirs comprising:
      at least one sample reservoir positioned in a first input defined by the microfluidic assembly;

14 a nucleic acid extraction matrix positioned in the microfluidic assembly and in fluid communication to an automated sample preparation (ASP) reservoir through a first flow channel defined by the microfluidic assembly,
   a waste reservoir defined within the microfluidic assembly;
   a fluid switching assembly configured to provide a first setting that permits flow from the first wash buffer reservoir through the nucleic acid extraction matrix and then to the waste reservoir and a second setting that permits collection of a nucleic acid-containing sample;
   an assay chamber in fluid communication with a third flow channel and with the waste reservoir through a fourth flow channel such that a labeled nucleic acid-containing sample flows through the assay chamber and then to the waste reservoir, wherein vibration-driven mixing agitates fluids while present in the assay chamber, wherein the labeled nucleic acid sample is mixed with a vibration motor that is proximate to a first side of the assay chamber, and air-filled cavities inside the assay chamber are in contact with an inner portion of the first side of the assay chamber, the vibration motor and the air-filled cavities configured to promote microfluidic mixing of fluid in the assay chamber.; and
   a nucleic acid-detecting microarray module positioned in the assay chamber, the method comprising:
   a) introducing a nucleic acid-containing sample into the ASP reservoir;
   b) flowing the nucleic acid-containing sample to the nucleic acid extraction matrix such that at least a portion of the nucleic acid sample adheres the nucleic acid extraction matrix;
   c) flowing the first wash buffer through the nucleic acid extraction matrix and then to the waste reservoir;
   d) flowing an elution buffer through the nucleic acid extraction matrix and then to an output collection vessel to collect a purified nucleic acid sample;
   e) removing or pumping purified nucleic acid sample from collection vessel to labeling apparatus;
   f) labeling the purified nucleic acid sample with a label to form a labeled nucleic acid sample;
   g) placing a vessel holding the labeled nucleic acid sample into the microfluidic assembly or pumping the labeled nucleic acid sample into the microfluidic assembly;
   h) flowing the labeled sample from the vessel holding the labeled nucleic acid sample through the assay chamber and then to the waste reservoir, wherein vibration-driven mixing agitates the labeled sample while present in the assay chamber and closed-loop thermal control maintains steady temperature in the assay chamber; and
   i) collecting data from the nucleic acid-detecting microarray module.

24. The method of claim 23, wherein the sample is a clinical human sample or an environmental sample.

25. The method of claim 23, wherein the third flow channel includes a first serpentine flow channel section and the fourth flow channel includes a second serpentine flow channel section.

26. The method of claim 23, wherein the plurality of reservoirs includes a second wash buffer chamber for holding a second wash buffer and a third wash buffer chamber holding a third wash buffer.

27. The method of claim 26 further comprising washing the assay chamber with the second wash buffer prior to introducing the labeled nucleic acid sample to the assay chamber.

28. The method of claim 26 further comprising washing the assay chamber with the third wash buffer after introducing the labeled nucleic acid sample to the assay chamber.

29. A mixing chamber comprising:
an assay chamber having a predetermined thickness and a first side having an outer surface and an inner surface, the assay chamber configured to receive a fluid therein;
a vibration motor affixed to or proximate to the outer surface of the assay chamber; and
a plurality of air-filled cavities in inside the assay chamber contacting the inner surface of the first side of the assay chamber, the vibration motor and the air-filled cavities configured to promote microfluidic mixing of fluid in the assay.

30. The mixing chamber of claim 29, wherein the predetermined thickness is from 10 to 200 micrometers.

31. The mixing chamber of claim 29, wherein the plurality of air-filled cavities have a circular cross sections.

32. The mixing chamber of claim 29, wherein the plurality of air-filled cavities are arranged in a square or rectangular array.

33. The mixing chamber of claim 29, wherein the plurality of air-filled cavities are slits.

34. The mixing chamber of claim 29, wherein the plurality of air-filled cavities include a combination of slits and openings having a circular cross sections.

16

*    *    *    *    *